(12) United States Patent
Medina et al.

(10) Patent No.: US 8,404,284 B2
(45) Date of Patent: Mar. 26, 2013

(54) MEDICINAL AND HERBAL COMPOSITION AND USES THEREOF

(75) Inventors: Maria Medina, Nairobi (KE); Paul Kiprono Chepkwony, Eldoret (KE); Mitchell Medina, Nairobi (KE)

(73) Assignee: International Patent Holdings LLC (KN)

( * ) Notice: Subject to any disclaimer, the term of this patent is extended or adjusted under 35 U.S.C. 154(b) by 235 days.

(21) Appl. No.: 12/977,635

(22) Filed: Dec. 23, 2010

(65) Prior Publication Data

US 2012/0164247 A1     Jun. 28, 2012

(51) Int. Cl.
*A01N 65/00*     (2009.01)

(52) U.S. Cl. ....................................................... 424/725
(58) Field of Classification Search ................... None
See application file for complete search history.

(56) References Cited

PUBLICATIONS

Broutin et al., Proc. R. Lond. B, (Suppl), 271; 2004, pp. S302-S305.*

* cited by examiner

*Primary Examiner* — Michael Meller
(74) *Attorney, Agent, or Firm* — Gary J. Gershik; Cooper & Dunham LLP

(57) ABSTRACT

The subject application provides compositions and methods for treating HIV/AIDS and other diseases. The compositions contain herbs or extracts of herbs found in Kenya, and naltrexone.

21 Claims, No Drawings

MEDICINAL AND HERBAL COMPOSITION AND USES THEREOF

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 7,556,830 and 7,674,483, and U.S. Application Publication No. 2009-0069277 A1 disclose compositions obtained from herbs and their uses, including in the treatment of infectious diseases. Applicants have continued human trials with the compositions of the aforementioned patents, and have made several improvements.

SUMMARY OF THE INVENTION

The subject application provides a pharmaceutical composition comprising:
root of *Dovyalis abyssinica* or an extract thereof;
root of *Clutia robusta* or an extract thereof; and naltrexone.

The subject application also provides a method for preparing the pharmaceutical composition disclosed herein, the method comprises steps of:
a) obtaining a mixture of the herb material;
b) boiling the mixture from step a) in water; and
c) filtering the water extract to obtain a filtrate.

The subject application yet further provides a method of treating an infectious disease in a patient comprising administering to the patient an effective amount of root of *Dovyalis abyssinica* or an extract thereof; root of *Clutia robusta* or an extract thereof; and naltrexone, so as to treat the infectious disease.

The subject application yet further provides a pharmaceutical composition for use in treating a patient with an infectious disease comprising root of *Dovyalis abyssinica* or an extract of any one thereof; root of *Clutia robusta* or an extract of thereof; and naltrexone.

DETAILED DESCRIPTION OF THE INVENTION

The subject application provides a pharmaceutical composition comprising:
root of *Dovyalis abyssinica* or an extract thereof;
root of *Clutia robusta* or an extract thereof; and naltrexone.

In an embodiment of the pharmaceutical composition, the pharmaceutical composition further comprises at least one of, or an extract of at least one of, stem bark of *Prunus africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, or root of *Periploca linearifolia*.

In another embodiment of the pharmaceutical composition, the pharmaceutical composition further comprises each of, or an extract of, stem bark of *Prunus africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

In yet another embodiment of the pharmaceutical composition, the pharmaceutical composition comprises dried root of *Dovyalis abyssinica*, dried root of *Clutia robusta*, or an extract of any one thereof.

In yet another embodiment of the pharmaceutical composition, the pharmaceutical composition comprises dried stem bark of *Prunus africana*, dried stem bark of *Croton macrostachyus*, dried stem bark of *Acacia nilotica*, dried root of *Rhamnus prunioides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, dried root of *Periploca linearifolia*, or an extract of any one thereof.

In yet another embodiment of the pharmaceutical composition, in the pharmaceutical composition the root of *Dovyalis abyssinica* and the root of *Clutia robusta*, whether dried or not, or an extract of each, are in a weight ratio of 1:1.

In yet another embodiment of the pharmaceutical composition, in the pharmaceutical composition the root of *Dovyalis abyssinica*, the root of *Clutia robusta*, the stem bark of *Prunus africana*, the stem bark of *Croton macrostachyus*, the stem bark of *Acacia nilotica*, the root of *Rhamnus prinoides*, the root of *Adenia gummifera*, the root of *Asparagus africanus*, the stem bark of *Anthocleista grandiflora*, the whole plant of *Plantago palmata*, the root of *Clematis hirsuta*, the stem bark of *Ekebergia capensis*, the stem bark of *Bersama abyssinica* and the root of *Periploca linearifolia*, whether dried or not, or an extract of each, are in a weight ratio of 2:2:2:2:2:2:1:2:2:1:2:2:2.

In yet another embodiment of the pharmaceutical composition, the pharmaceutical composition is in a unit dose having an amount of herb material of approximately 250 mg.

In yet another embodiment of the pharmaceutical composition, the pharmaceutical composition comprises the extract of the herb material, whether dried or not.

In yet another embodiment of the pharmaceutical composition, in the pharmaceutical composition the extract is a water extract.

In yet another embodiment of the pharmaceutical composition, in the pharmaceutical composition the amount of naltrexone is 0.1 mg to 10 mg, inclusive, preferably 1 mg to 8 mg, inclusive, more preferably 4 mg to 6 mg, inclusive.

The subject application also provides a method for preparing the pharmaceutical composition disclosed herein, the method comprises steps of:
a) obtaining a mixture of the herb material;
b) boiling the mixture from step a) in water; and
c) filtering the water extract to obtain a filtrate.

The subject application yet further provides a method of treating an infectious disease in a patient comprising administering to the patient an effective amount of root of *Dovyalis abyssinica* or an extract thereof; root of *Clutia robusta* or an extract thereof; and naltrexone, so as to treat the infectious disease.

In an embodiment of the method, the method comprises further administering to the patient an effective amount of at least one of, or an extract of at least one of, stem bark of *Prunus africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, or root of *Periploca linearifolia*.

In another embodiment of the method, the method comprises further administering to the patient an effective amount of each of, or an extract of, stem bark of *Prunus africana*, stem bark of *Croton macrostachyus*, stem bark of *Acacia nilotica*, root of *Rhamnus prunioides*, root of *Adenia gummifera, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

In yet another embodiment of the method, the method comprises administering to the patient an effective amount of dried root of *Dovyalis abyssinica*, dried root of *Clutia robusta*, or an extract of any one thereof.

In yet another embodiment of the method, the method comprises administering to the patient an effective amount of dried stem bark of *Prunus africana*, dried stem bark of *Croton macrostachyus*, dried stem bark of *Acacia nilotica*, dried root of *Rhamnus prunioides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, dried root of *Periploca linearifolia*, or an extract of any one thereof.

In yet another embodiment of the method, the root of *Dovyalis abyssinica* and the root of *Clutia robusta*, whether dried or not, or an extract of each, are in a weight ratio of 1:1.

In yet another embodiment of the method, the root of *Dovyalis abyssinica*, the root of *Clutia robusta*, the stem bark of *Prunus africana*, the stem bark of *Croton macrostachyus*, the stem bark of *Acacia nilotica*, the root of *Rhamnus prinoides*, the root of *Adenia gummifera*, the root of *Asparagus africanus*, the stem bark of *Anthocleista grandiflora*, the whole plant of *Plantago palmata*, the root of *Clematis hirsuta*, the stem bark of *Ekebergia capensis*, the stem bark of *Bersama abyssinica* and the root of *Periploca linearifolia*, whether dried or not, or an extract of each, are in a weight ratio of 2:2:2:2:2:2:1:2:2:1:2:2:2:2.

In yet another embodiment of the method, the herb material is administered in a unit dose having an amount of herb material of approximately 250 mg.

In yet another embodiment of the method, the extract of the herb material is administered, whether the herb material is dried or not.

In yet another embodiment of the method, the extract administered is a water extract.

In yet another embodiment of the method, the amount of naltrexone administered is 0.1 mg to 10 mg, inclusive, preferably 1 mg to 8 mg, inclusive, more preferably 4 mg to 6 mg, inclusive.

The subject application yet further provides a pharmaceutical composition for use in treating a patient with an infectious disease comprising root of *Dovyalis abyssinica* or an extract of any one thereof; root of *Clutia robusta* or an extract of thereof; and naltrexone.

In an embodiment of the pharmaceutical composition, the pharmaceutical composition further comprises at least one of, or an extract of at least one of, stem bark of *Prunus africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, or root of *Periploca linearifolia*.

In another embodiment of the pharmaceutical composition, the pharmaceutical composition further comprises each of, or an extract of, stem bark of *Prunus africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

In yet another embodiment of the pharmaceutical composition, in the pharmaceutical composition the amount of naltrexone is 0.1 mg to 10 mg, inclusive, preferably 1 my to 8 mg, inclusive, more preferably 4 mg to 6 mg, inclusive.

By any range disclosed herein, it is meant that all hundredth, tenth and integer unit amounts within the range are specifically disclosed as part of the invention. Thus, for example, 0.01 mg to 10 mg means that 0.02, 0.03 . . . 0.09; 0.1, 0.2 . . . 0.9; and 1, 2 . . . 10 mg unit amounts are included as embodiments of this invention.

The objects of the instant invention include:

Compositions for and methods of preventing and/or alleviating of Immune Reconstitution Syndrome associated with the use of the herbal compositions of U.S. Pat. No. 7,556,830.

Compositions for and methods of preventing and/or alleviating toxic effects of the herbal compositions of U.S. Pat. No. 7,556,830 and increasing the effectiveness thereof.

Compositions for and methods of treating HIV infection in cases of drug resistance to Highly Active Anti-Retroviral Therapy (HAART), or in conjunction therewith.

Compositions for and methods of presumptive diagnosis of tuberculosis or TB reinfection/reactivation in patients using the herbal compositions of U.S. Pat. No. 7,556,830 in a resource-poor setting with dual high prevalence rates of tuberculosis/HIV infection, when Mantoux tests are non-reactive and chest x-rays show negative findings, especially in Stage IV HIV infection.

Compositions for and methods of treating Herpes zoster (shingles) and Herpes simplex (oral and genital infections) with the herbal compositions of U.S. Pat. No. 7,556,830.

Compositions for and methods of treating Kaposi's sarcoma with the herbal compositions of U.S. Pat. No. 7,556,830.

A novel composition and method of treating HIV/AIDS and other infectious diseases is provided, comprising extracts of herbs found in Kenya, and a known allopathic medicine, naltrexone, which has never been used in this combination for this purpose.

The chemical structure and properties of naltrexone is as follows:

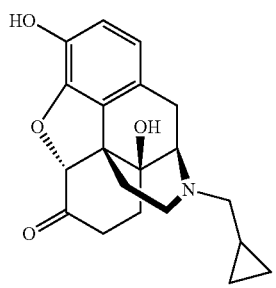

Naltrexone (Systematic (IUPAC) name 17-(cyclopropylmethyl)-4,5α-epoxy-3,14-dihydroxymorphinan-6-one)

| | |
|---|---|
| CAS number | 16590-41-3 |
| ATC code | N07BB04 |
| PubChem | CID 5360515 |
| IUPHAR ligand ID | 1639 |
| DrugBank | APRD00005 |

| | |
|---|---|
| ChemSpider | 4514524 |
| UNII | 5S6W795CQM |
| Chemical data | |
| Formula | C$_{20}$H$_{23}$NO$_4$ |
| Mol. mass | 341.401 g/mol |
| SMILES | eMolecules & PubChem |
| Physical data | |
| Melt. point | 169° C. (336° F.) |
| Pharmacokinetic data | |
| Bioavailability | 5-40% |
| Protein binding | 21% |
| Metabolism | Hepatic |
| Half-life | 4 h (naltrexone); 13 h (6-β-naltrexol) |
| Excretion | Renal |
| Therapeutic considerations | |
| Pregnancy cat. | Category B3 (Australia) |
| Legal status | Schedule 4 (Australia) |
| Routes | Oral; hepatic |

Naltrexone is an opioid receptor antagonist used primarily in the management of alcohol dependence and opioid dependence. (Source: http://en.wikipedia.org/wiki/Naltrexone).

Low-Dose Naltrexone (LDN), a therapy in which naltrexone is used in doses approximately one-tenth of those used for drug/alcohol rehabilitation purposes, is being used as an "off-label" treatment for certain immunologically-related disorders. (Source: http://en.wikipedia.org/wiki/Low-dose_naltrexone). The normal dose of naltrexone used to treat drug addiction is about 50 mg. Low-dose naltrexone (LDN) from 3 mg to 5.0 mg has been proposed in the literature. In Applicants' instant experiment, LDN is a dose of naltrexone that is less than 10 mg.

DEFINITIONS

As used in this application or in connection therewith, the following terms have the meanings herebelow given.

1. AIDS—(Acquired Immune Deficiency Syndrome) can be a colloquial shorthand for the entire course of the HIV/AIDS illness, or, in context, may refer more specifically to Stage 4 of 5 of that illness, which stage is characterized by HIV-positive tests with CD4 count less than 200 cells/μL, or CD4+ cells less than 14% of total (WBC) white blood cell count.

Stage 4 is associated with the following clinical manifestations:

Presenting clinical conditions where a presumptive diagnosis can be made on the basis of clinical signs or simple investigations:
   a) HIV wasting syndrome
   b) Pneumocystis pneumonia
   c) Recurrent severe or radiological bacterial pneumonia
   d) Chronic herpes simplex infection (orolabial, genital or anorectal of more than one month's duration)
   e) Oesophageal candidiasis
   f) Extrapulmonary Tuberculosis
   g) Kaposi's sarcoma
   h) Central nervous system toxoplasmosis
   i) HIV encephalopathy
   Presenting clinical conditions where confirmatory diagnostic testing is necessary:
   a) Extrapulmonary cryptococcosis including meningitis
   b) Disseminated non-tuberculous mycobacteria infection
   c) Progressive multifocal leukoencephalopathy
   d) Candida of trachea, bronchi or lungs
   e) Cryptosporidiosis
   f) Isosporiasis
   g) Visceral herpes simplex infection
   h) Cytomegalovirus (CMV) infection (retinitis, or infection of an organ other than the liver, spleen or lymph nodes)
   i) Any disseminated mycosis (e.g. histoplasmosis, coccidiomycosis, penicilliosis)
   j) Recurrent non-typhoidal salmonella septicaemia
   k) Lymphoma (cerebral or B cell non-Hodgkin)
   l) Invasive cervical carcinoma
   m) Visceral leishmaniasis (The foregoing definition 1 is adapted from "Revised World Health Organization (WHO) Clinical Staging of HIV/AIDS for Adults and Adolescents" (2005)) [cited in 2, 18 & 21].

2. ALT or SGPT—Alanine amino transferase or Serum glutamic pyruvic transaminase is an enzyme specific to liver and heart cells; elevated levels in the serum mean liver or heart inflammation or cellular damage to these organs.
3. BID—twice a day (bis in die).
4. Bioline, Determine & Unigold are brands of HIV screening test kits.
5. CD4+ cells are a type of white blood cells that HIV attacks.
6. ESR stands for Erythrocyte Sedimentation Rate, which is a non-specific quantitative test for inflammation. Normal ESR levels for adults are: for males—less than 10 mm/hr; for females—less than 15 mm/hr.
7. HAART stands for Highly Active Antiretroviral Treatment, which is a treatment regimen of preferably at least 3 anti-retroviral drugs to effectively suppress Human Immunodeficiency Virus (the actual number of antiretroviral drugs comprising the HAART "cocktail" may vary).
8. HC stands for herbal capsule, comprising the composition of U.S. Pat. No. 7,556,830.
9. HIV is the Human Immunodeficiency Virus
10. IRIS stands for Immune Reconstitution Inflammatory Syndrome, which is a critical stage in the treatment of HIV disease consisting of a constellation of exaggerated signs and symptoms as a result of the immune system's improved capability of mounting a response in its detection of a previously occult infection or of non-infectious antigens present in the body.
11. LDN stands for Low Dose Naltrexone, which is roughly one-tenth of the dose of those used for drug/alcohol rehabilitation purposes. More specifically, LDN comprises daily doses between 0.5 mg and 10 mg per day regardless of body weight, inclusive. The regular drug/alcohol rehabilitation dose is 50 mg/per day regardless of body weight. The range of the effective dose for certain immunologically-related disorders is reported to be from 1.5 to 6.5 mg (Bihari).[13] Various studies have suggested different optimum doses for various conditions.

Some internet bloggers claim in that LDN doses lower than 1.5 can be effective.

12. Lypodystrophy is a derangement in the fat distribution of the body. The condition is one of the side-effects of anti-retrovirals. Lypodystrophy is described clinically as a decrease in facial fat and the formation of a "buffalo hump".
13. Mantoux test is a skin test using particles from the tubercle bacilli to determine the presence of tuberculosis infection. Results are interpreted as positive or negative based on the diameter of a defined reaction on the skin (a wheal). A more accurate test is the TB spot test which can measure active and latent infections.

14. OD means once a day (omne in die)
15. ORS stands for oral rehydration solution
16. Phytoalexins are plant chemicals, some of which appear to have therapeutic properties in humans, which are produced when the plant is "stressed", or is in an unfavorable environment or under severe conditions e.g., extreme weather, pest infestations or at high altitudes.

Three major types of phytoalexins are alkaloids, terpenoids and glycosteroids.

Although some scientists differentiate phytoalexins (which are not pre-formed, but only produced in nature during stressful conditions or during plant injury) from phytoanticipins (which are pre-formed, to protect the plant whether the stressful conditions occur or not), we will be using the term phytoalexins to cover both classes of substances, because the chemical components of the Applicants' inventions are derived from plants that were gathered from an area of high altitude as discussed in U.S. Pat. No. 7,556,830. A plurality of the suspected active ingredients isolated thus far by Applicants may not be found in the same herbs at lower altitudes.

17. PTB stands for Pulmonary tuberculosis.
18. TID means thrice a day (ter in die).
19. WBC/HPE means white blood cells per high power field.
20. Kaposi's sarcoma is a malignancy associated with human herpesvirus 8 (HHV8) infection. It appears as discolored (purplish, brownish, black or reddish) raised lesions of varying sizes often found on the skin, though they can be visceral or elsewhere in the body.

The instant invention will be better understood from the experimental details which follow. However, one skilled in the art will readily appreciate that the specific methods and results discussed are merely illustrative of the invention as described more fully in the claims which follow thereafter.

Experimental Details:

Applicants have continued to test the compositions and methods of U.S. Pat. Nos. 7,556,830 and 7,674,483, and U.S. Patent Application Publication No. 2009-0069277 A1.

The subjects are patients who have been initially screened by the Voluntary Counseling Center (VCT) Program of a government registered community-based organization in the Sinai section of the Mukuru slums near the Industrial Area of Nairobi, Kenya.

Mukuru, a 500 square-kilometer slum area, is an informal settlement in the east of Nairobi, is occupied by a population of 400,000. The population consists mostly of squatters, who work, work casually, or not at all, in various locations and parts of Nairobi, chiefly the Industrial Area. Mukuru is divided into five villages: Kwajenga, Reuben, Vuatanya, Viwandani and Kayaba. The VCT which hosts the instant experiment is located in the outer section of Sinai in the village of Viwandani, which is further subdivided into sections called: Sinai, Paradise (ironically), Lunga-Lunga, and Jamaica.

Mukuru Viwandani, where Sinai is located, has no government health facility, water system, sewer system, or any kind of infrastructure. Water (of widely varying purity, quality, sanitariness and toxicity) is bought from various vendors, or collected from rain (with equally variable results). A few enterprising individuals have managed to illegally get connected to the city water supply and electricity, both of which are themselves of uneven quality.

The eleven-year old VCT program which houses the present experiment comprises a primary school, a twenty-four-hour operating out-patient clinic, a birthing center with a 5-bed maternity ward, and an orphanage that is partially funded by the government, churches, non-government organizations and well-wishers. Its twenty-four-hour out-patient clinic also comprises a TB treatment center which inventor Dr. Maria Medina helped open in 2005, and an HIV Prevention from Mother to Child Transmission Program Center (PMTCT). The community-based organization which houses these programs also provides free vaccines provided by the Kenyan Ministry of Health for children in the community.

The patient population served by the host clinic is 80% female. The diseases endemic in the area are typhoid, infectious diarrhea, respiratory infections, malaria, HIV/AIDS, and other sexually transmitted diseases. There are episodic cholera outbreaks. Life expectancy in Mukuru is considerably less than the Kenyan national average of 49 years.

The Mukuru slums are occupied illegally by people who have migrated from their respective rural homes to find jobs in Nairobi. People live mostly in shacks with metal sheet roofing. Sixty percent of the population are under eighteen and many of all ages do not have adequate skills to earn a living. They therefore are either unemployed and/or engage in prostitution, vices and/or various criminal activities.

In the present experiment, an aqueous solution of the herbal remedy of U.S. Pat. No. 7,556,830 was made into capsule form by the removal of water from the concentrated extract with a rotary evaporator, though other methods of concentration will occur to those skilled in the art. The administration of the resulting powder, in its more concentrated form, produced certain transient irregularities in HIV-positive individuals who are being treated. The present invention addresses the mitigation of those irregularities and improvement of the efficacy of the invention of U.S. Pat. No. 7,556,830.

A decrease in dosage was not a mitigating solution transient irregularities. The herbal remedy in the former dose used in the experiment of U.S. Pat. No. 7,556,830 was the concentration of the active ingredients ratio in the supernatant liquid of tablespoon of boiled herbs in 150 cc of water. A patient in Applicants' prior experiment in rural Kericho received about half of herbal component of the current capsule preparation, which contains 248 to 250 mg in a 500 mg capsule (HC). The prior preparation does not seem to be as efficacious as the more concentrated dose in the instant HC form, for populations whose immune system is constantly being challenged, such as the group in the present experiment.

A follow-up HIV screening by a laboratory technologist from the Kenya Medical Research Institute, performed on some of the patients in the first experimental group of U.S. Pat. No. 7,556,830 showed that several more patients within that group had turned HIV-negative.

Applicants hypothesized that an apparently slower response by subjects to the herbal therapy of U.S. Pat. No. 7,556,830 was a result of Immune Reconstitution Inflammatory Syndrome, triggered by the large boost to the subjects' immunological from the more concentrated and higher dose employed in the present experiment. IRIS is a manifestation that the therapy (i.e HC or HAART) is actually working, and that the patient's immune system is responding too fast and/or too strongly to infectious agent(s) or antigen(s) already present in the body, or attacking it from the environment, the more active immunological response occurring as a result of the therapy.

The IRIS phase will sometimes pass without additional therapy. However, it can also result in morbidity. In any event, the manifestation of IRIS is a critical stage in treatment of HIV/AIDS because high grade fever develops for several days or weeks and can cause weakness and severe dehydration. IRIS seems to occur more frequently in subjects under Applicants' HC therapy than with HAART, because HC therapy seems to be producing faster and more radical gains in CD4 counts and other markers of otherwise beneficial effects in the treatment of HIV/AIDS in Applicants' instant experiment than are typically experienced with HAART, subject to further statistical analysis. A range of possible mitigations was attempted, culminating in the successful deployment of naltrexone, specifically Low Dose Naltrexone (LDN) as a part of the therapy.

Although there have been studies using LDN, these therapies are focused on the use of LDN for the treatment of Crohn's Disease, Irritable Bowel Syndrome, Multiple Sclerosis, autism and various autoimmune diseases.[13, 16 & 17] Presently, a clinical trial in Mali, which started in 2008, is being conducted by Dr. Jaquelyn McCandless on HIV-positive individuals using HAART and LDN in combination, and separately, aims to preventing AIDS and lipodystrophy,[15]. McCandless has not used Applicants' herbal composition. It has been stated by Bihari[14] that deployment of LDN alone on HIV+ subjects does not increase CD4 count, but only maintains its level or delays its decrease.

HAART's goal is to effectively suppress the virus, and its commencement is limited by certain guidelines of the WHO. These guidelines are based on the clinical state of the subject, including the presence of opportunistic infection, the level of the subject's CD4 count, and viral load levels. These criteria are intended to prevent the development of resistant strains of the virus and to minimize the development of adverse and toxic effects, which are almost always quite serious with HAART, especially in nutritionally- and environmentally-challenged people.

Further, the side-effects of HAART also include characteristic physical changes that can be irreversible and make it obvious to some eyes that the HAART-using subject is HIV-positive. These HAART-induced changes can trigger the stigma which many persons living with HIV/AIDS strongly desire to avoid. [2, 4, 6, 7, 15 & 18].

Our various inventions have been tried at every stage of the HIV/AIDS disease. A few patients in the prior rural Kericho experiment who had been taking the herbs by drinking the supernatant liquid of U.S. Pat. No. 7,556,830 have now turned HIV-negative after starting the herbs in capsule form and have shown no visible permanent or severe adverse reactions. Some of those who turned HIV-negative and discontinued taking the herbs have remained HIV-negative. However, the patients in the prior experiment are in a rural setting and are mostly farmers. The patients are also mostly of the Kalenjin tribe whose members are more traditionally-oriented and therefore less likely to engage in risky sexual behavior. Further, they also live in less densely-populated areas and are therefore less likely to be exposed to opportunistic infections from others.

Herbal Remedy (U.S. Pat. No. 7,556,830)+LDN to Prevent or Alleviate IRIS

Naltrexone, a pure μ opioid antagonist, in small doses, is known to modulate the responses of the immune system. Naltrexone is very valuable in combination with the compositions of our U.S. Pat. No. 7,556,830 in restoring balance to the function of the immune system. This is especially useful for HIV/AIDS patients with a very low CD4 count and/or a heavy viral load, who experience deranged responses of the immune system as it regains its normal function under the stimulus of said herbal compositions. The addition of LDN to the treatment regimen in the instant experiment mitigates or prevents Immune Reconstitution Inflammatory Syndrome. HAART is not known to boost the immune system to the degree that the compositions of U.S. Pat. No. 7,556,830 do. IRIS is an issue in 258-35% of cases with HAART, in non-resource-poor settings. The goals of the instant invention include achieving a progressive increase in CD4 levels, mitigating erratic CD4 level changes and boosting CD4 levels in patients whose CD4 counts remain below 500 cells/μL.

Immune Reconstitution Inflammatory Syndrome, as defined above, consists of a wide variety of exaggerated symptoms as result of the human immune system's improved capability of detecting and fighting infection/infections, or as a response to the immune system detecting non-infectious antigenic particles. IRIS has been observed in patients taking HAART, especially in patients with low CD4 cell levels, which low levels can provide a platform for rapid elevation of CD4+ cells or rapidly improved immune function [19 & 20]. However, IRIS is a rare occurrence in resource-poor settings such as Kenya, because HAART is not commonly known to cause a rapid increase in the CD4 cell levels in most Kenyan patients, nor does HAART apparently cause elevations of CD4 count as rapidly as the compositions of U.S. Pat. No. 7,556,830, anywhere.

The compositions of U.S. Pat. No. 7,556,830 alone, and the more so when taken in one capsule (HC) OD or BID doses can significantly elevate absolute CD4 cell counts from a few cells up to more than five hundred cells within a week, but in some patients the levels can be erratic. This elevation caused by the herbal remedy is quite impressive. Most patients in HAART in Kenya do not even show an increase in their CD4+ levels until after months of treatment and some patients even take a year to experience a small elevation in their CD4 cell count. Moreover, in some studies in the United States, the average increase is no more than fifty cells+ within weeks, and then a further fifty to a hundred a year [2].

According to Ratnam et. al. [19], in the U.S., where patients in general receive a better standard of care, the incidence of IRIS in conjunction with HAART is as high as twenty-five percent but no standard protocol for the treatment, prevention and alleviation of IRIS has been developed.

One obvious hypothesis for the explanation of the exaggerated symptoms of IRIS that occur in conjunction with Applicants' HC therapy is a derangement of the white blood cell subsets ratios, with different functions in the immune cascade of events occurring when one subset is becomes depleted, thus effecting an abnormal response of the immune system in the presence of an antigen. Although there are various other possible mechanisms that could explain why IRIS occurs and why it does in some subjects and not in others, the imbalance of the white blood cell subsets is most apparent in patients who have very low CD4 cell counts [2, 6, 15, 19 & 21]. That may also be the reason why other immunologic derangement syndromes are associated with HIV, and manifest as allergic reactions, autoimmunity syndromes and cancers (i.e. Kaposi's Sarcoma), which last, especially, has higher incidence in persons who are living with HIV infection than in individuals who are not.

Rogers et. al. [22] described an IRIS case which manifested in the form of fulminant myocarditis. After Applicants' first mortality due to IRIS in the instant experiment, we discovered the use of LDN as a conjunctive therapy, and have since diagnosed four cases of a very mild form of the same condition. All four subjects of the instant experiment had no previous heart condition and were started with the HC alone, but were given LDN after the first mortality had occurred. All four patients did not develop fever and their conditions did not progress to more fulminant forms. All four responded promptly to either digoxin or furosemide. More importantly, none of the other subjects developed IRIS once LDN was combined with the HC for about seven months, even though most of the patients harbor comorbid infections like tuberculosis and herpes.

Impaired Kidney Function—Plan: Decrease Herbal Remedy Dose+LDN

The observed toxic effect of high doses (greater than 10 mg/kg/day of the active ingredients of the herbal remedy U.S. Pat. No. 7,556,830) is the elevation of creatinine levels. In cases where high doses improve the CD4 level, but kidney toxicity is observed, LDN is helpful in potentiating the effects of the herbal remedy when the HC's dose needs to be decreased.

Herbal Remedy+LDN=No CD4 Increase, or Decrease in CD4: Rule Out Tuberculosis or Other Opportunistic Infection or Reinfection We observed in a few patients that CD4 count does not increase with the HC and LDN combination, even in the presence of marked clinical improvement. In such cases, one is almost sure that either there is an undiagnosed opportunistic infection (frequently TB in the setting of the instant experiment), and/or, the patient is not complying with the use of barrier contraception that is mandated for subjects of the instant experiment. Obviously, Applicants cannot actually observe whether barrier contraception is actually being used by subjects of the experiment. But when subjects' CD4 values fail to improve, they frequently admit their failure to use barrier contraception consistently, when they are confronted by Applicants with questions as to whether they use barrier protection consistently.

The decision to initiate empirical treatment for tuberculosis rests with the physician. So far, no test for tuberculosis in patients with AIDS has reached a satisfactory sensitivity in accurately screening patients with the infection. According to Githui et. al.[10], the probability of successfully finding Mycobacterium bacilli in a sputum exam is only 8.8% to 46.6% positive results in patients suspected to have tuberculosis. The Mantoux test may also be non reactive in patients at stage of HIV infection. Chest X-rays are of no use in tuberculosis of the lymph nodes, which is not a rare condition in Kenya. Certain assay tests, such as that by Oxford Immunotec (UK) (www.oxfordimmunotec.com), have a better but still unsatisfactory reliability of 87.5% in patients whose CD4 count is below 100 cells/μL, according to correspondence of that entity with Applicants. The OxfordImmunotec assay test is also expensive, and unavailable in resource-poor Kenya.

Once compliance of the patient with the use of barrier contraception has been established (to the degree possible), the persistence of failure of a given subject's CD4 to elevate, in an area where TB is endemic, is most probably caused by TB. Once TB is empirically treated, Applicants have observed that the subject's CD4 count goes up.

Herbal Capsule+LDN Treatment for Treatment of Shingles or Oral or Genital Herpes We also observed that, once the patients' normal immune system function is restored with HC & LDN, a variety of viral infections associated with HIV/AIDS, e.g., shingles, and oral and genital herpetic lesions, resolve spontaneously. All of the seven patients who developed either varicella or herpetic lesions had them dry out in a week's time and none have observably recurred since the subjects have been taking HC+LDN. The patients under treatment also describe the sensation associated with now non-manifest breakouts as less intense than during their past eruptions or sometimes previously described just a tingling sensation previously before the eruption of the vesicular lesions. The sensation associated with new potentially-incipient vesicular break outs can now easily be managed with 500 mg of paracetamol TID for those under the instant treatment. Although treatment with HC alone would have produced similar results, LDN is still needed, as this type of infection associated with HIV/AIDS can precipitate IRIS. One cannot know if there is a latent infection unless antigen or antibody assays are done. These tests are not available or too expensive in a resource-poor setting.

Herbal Capsule+LDN Treatment for Treatment of Kaposi's Sarcoma

Two patients who had Kaposi's sarcoma who started the herbal remedy showed dramatic resolution of their lesions. One had Kaposi's lesions all over his body. In two weeks' time all the lesions were gone. One had lesions on both of his forearms. In less than a week they were gone.

The association of Kaposi's malignancy with Human herpes virus 8 infection has been established[12] and would probably explain why both patients promptly responded to the HC+LDN therapy.

Eligibility for the Experiment

Eligibility Criteria:
  Male or non-pregnant female 18 to 50 years old
  Have the ability to understand informed consent and to comply with the procedures.
  HIV+ on both screening and confirmatory tests, at any stage, with or without the presence of opportunistic infections.
  Should be willing to use barrier method of contraception at every sexual encounter.
  Should be willing not to abuse alcohol or any form of recreational drugs.

Methodology

The screening test kit brands we use are the Determine and Bioline test kits. In cases where the results of the two kits are weak positive results, Unigold is also used. All three kits are also used in all Voluntary Counseling and Testing Centers (VCT's) all over Kenya.

Upon admission to the program, to give a head start to these patients whose nutrition is universally deficient, each patient is given a week's supply of multivitamins, vitamin B complex, iron supplements and 960 mg cotrimoxazole tablets. The cotrimoxazole dose was later decreased to single strength or 480 mg daily, when several patients developed bone marrow suppression. The incidence of *Pneumocystis carinii* or *jiroveci* infection in Africa is lower compared to that in Europe and the U.S.[1]; and Zambia has used either double or single-strength doses[14]. There have been studies using the single strength dose successfully to prevent opportunistic infections in other immunocompromised conditions[5, 14 & 23].

Each patient also receives two to three kinds of the following foodstuffs: spinach, guavas, eggs, milk, cow peas, sweet potatoes, squash, maize flour, beans, rice or omens (local anchovies). Each patient is also individually evaluated for other health problems and given the appropriate remedy(ies) and advice.

As in HAART treatment, laboratory test results of patients who are clinically ill or have an opportunistic infection are only used as diagnostic tool and to evaluate the success of treatment for such condition. The parameter for progress (absolute CD4 count) in treatment is recorded regularly, including when the patient is clinically well and any opportunistic infection has been adequately treated.

Patients were tested weekly for progress and toxicities. We then determined a dose which can be tolerated by most of the patients, and recruited more subjects. In a preferred embodiment, two HC's (one each, B.I.D) approximately equal to 500 mg of the active ingredients of U.S. Pat. No. 7,556,830 per day, are administered. However, adjustments must be made according to the body weight of the subject, and lesser or higher dosages of as low as 100 mg and as high as 1 g, can be deployed. As a majority of the patients' health improved, we progressively scheduled their appointments further apart, to once every two weeks, and then, on a monthly basis.

Applicants are presently treating 28 to 30 patients out of the original 34 subjects we recruited. Four subjects became pregnant, two once, one twice and one thrice despite our constant reminders of the necessity of using a barrier method of contraception, and our consistent practice of making free male and female condoms available at all times. One important factor affecting compliance with the use of barrier protection is the lack of empowerment of female patients to say no to their partners when their partners refuse to use barrier protection. Many Kenyan men refuse to use condoms and some will become violent towards their partner when they are requested to use condoms. Five female patients have complained that their partners will not use condoms.

We lost one to patient due to IRIS precipitated by pulmonary tuberculosis infection (PTB, as defined above) and six patients have been lost to follow up, in some cases because of exclusion from the instant experiment because of failure to comply with its conditions. After contemplating the ethical dilemma accompanying exclusion, we subsequently retained two patients who became pregnant. One was retained because of a dramatic rise in her CD4 (see Example 3B). The other was retained because she is a single mother of three children. No subjects developed IRIS or became bed-ridden at our last observation. Only one patient had become febrile, in that particular case, due to severe amebiasis.

The compositions of U.S. Pat. No. 7,556,830 were used on some pregnant women by in the prior study, and there have been no observed abnormalities reported in the progeny after delivery.

Normal reference values of relevant blood chemistry are as follows.

Creatinine (mg/dl): Normal=0.6-1.1 mg/dl

ALT or SGPT: Normal=7-56 u/L

Normal reference values of a key blood cellular component in the diagnosis and course of the HIV/AIDS illness is as follows.

CD4 (cells/µL) levels: Normal=500-1500 cells/µL

Example 1

Herbal Remedy without LDN

H. K., is a 34 year-old married electrician from Jamaica, Viwandani. He initially was tested HIV-positive. He had no health problems at that time, but was suspicious that he got infected from a sexual encounter with a female friend. His wife is upcountry in rural Kenya and is HIV-negative. He was never started on LDN because his initial CD4 was within normal levels (556 cells/µL) and he had no subjective complaints during his intake. His absolute CD4 count remains in the upper 500's to lower 600's range from the start of treatment through the last observation. His creatinine and ALT were always within the normal range. He was diagnosed to have recurrent malaria infection at last observation.

| H.K. ♂ | Start of Treatment | 1 month of treatment | 2 months of treatment | 3 months of treatment | 4 months of treatment | 5 months of treatment | 6 months of treatment | 7 months of treatment |
|---|---|---|---|---|---|---|---|---|
| Educ.: Form 4 | Baseline | 1 HC cap BID 9 mg/kg/day | 1 HC cap BID 9 mg/kg/day | 1 HC cap BID 9 mg/kg/day | 1 HC cap BID 9 mg/kg/day | | 1 HC cap BID 9 mg/kg/day | |
| CD4 | 556 cell/uL Creatinine = 1 mg/dl ESR = 2 mm/hr ALT = 11 µ/L | 477 cells/uL | 554 cells/µL | 618 cells/µL | 578 cells/µL | 589 cells/µL ALT = 16 µ/L | 610 cells/uL Creatinine = 0.7 mg/dl ESR = 1 mm · hr | 638 cells/µL |

Example 2

Herbal Remedy+LDN

A) C. O., a hawker, from Mukuru Reuben, was admitted to the program without any complaints. He was diagnosed through the PMTCT program when his wife started prenatal examination. He was started on LDN when his CD4 count fluctuated. C. O. never developed IRIS from start of treatment through more than eight months and his CD4 remained in the upper 900's and lower 1000's.

C. O. travels regularly to Nyanza Province which has a high malaria prevalence rate. The Western and Nyanza provinces of Kenya harbor the four species of parasites (*P. falciparum, P. vivax, P. ovale* & *P. malariae*) that cause malaria. C. O. has had recurrent malaria infection and has to be monitored for this problem.

At four and a half months after the start of treatment, a repeat HIV screening was done, with weak positive results on Determine, Unigold & Bioline. At seven months after the start of treatment, the results were negative on. Determine and weak positive on Bioline & Unigold.

| C.O. ♂ | Start of Treatment | 1 month of treatment | 2½ months of treatment | 3½ months of treatment | 4 months of treatment | 5½ months of treatment | 8 months of treatment |
|---|---|---|---|---|---|---|---|
| Educ: Form 4 | Baseline | 1 cap TID = 10.4 mg/kg/day | 1 cap BID = 13.88 6.94 mg/kg/day | 1 cap TID + LDN = 10.71 mg/kg/day | 2 caps OD + LDN = 6.94 mg/kg/day | 1 cap BID + LDN = 6.94 13.88 mg/kg/day | 1 cap BID + LDN = 6.9413.88 mg/kg/day |

-continued

| C.O. ♂ | Start of Treatment | 1 month of treatment | 2½ months of treatment | 3½ months of treatment | 4 months of treatment | 5½ months of treatment | 8 months of treatment |
|---|---|---|---|---|---|---|---|
| CD4 & Creatinine | 464 cells/uL 1.0 mg/dl | 1027 cells/μL 1.6 mg/dl | 731 cells/μL 0.6 mg/dl | 997 cells/μL 1.2 mg/dl ESR = 40 mm/hr | 977 cells/μL 1.0 mg/dl- ESR = 1 mm/hr | 1154 cells/μL 1.1 mg/dl ESR = 0 mm/hr | 1003 cells/μL |

B) F. M., a 41 year-old married female from Umoja, a town about three miles from Mukuru, was initially tested HIV positive. She got tested because she experienced on-and-off malaise. She claimed her CD4 was 295 cells/μL when she was initially tested.

On intake, her presenting symptoms were on-and-off headache, night sweats and chest congestion. She was admitted to the program about two years after initially testing HIV positive, and around three months later her CD4 count decreased and she began having recurrent urinary tract infections. Despite being advised to use condoms with her partner without fail, she claimed that her partner does not like to use protection.

Example 3

Herbal Remedy+HAART+LDN

A) E. N.1 is a 41 year-old community mobilizer of a HIV program (that of Applicants), and persistently insisted for three weeks on joining the instant experimental group. We initially did not enroll her because she has been taking HAART the staduvidine, nevirapine and lamivudine combination) tablets twice a day and her screening creatinine level was elevated. She was diagnosed as HIV-positive because she

| Dates | Start of Treatment | 1½ month of treatment | 3 months of treatment | 4 months of treatment | 4½ months of treatment | 6 months of treatment | 8½ months of treatment |
|---|---|---|---|---|---|---|---|
| F.M. ♂ Educ: Form 2 Weight = 77 kg | | 2 cap TID = 19.48 mg/kg/day | 1 cap OD = 3.24 mg/kg/day | 1 cap TID = 9.74 mg/kg/day | 1 cap BID = 6.49 mg/kg/day + LDN | 1 cap BID = 6.49 mg/kg/day + LDN | 1 cap BID = 6.49 mg/kg/day + LDN |
| CD4 & Creatinine | 432 cells/uL 1.2 mg/dl Baseline | 385 cells/μL 2.0 mg/dl | 322 cells/μL 1.0 mg/dl | 358 cells/μL 1.4 mg/dl ESR = 100 mm/hr | 476 cells/μL 0.8 mg/dl ESR = 30 mm/hr | 482 cells/μL 1.0 mg/dl ESR = 45 mm/hr | 823 cells/μL |

C) R. A., a 31 year-old married domestic worker from Mukuru Njenga, was initially diagnosed to be HIV positive on August 2006 through the PMTCT program. Upon admission to the program, her only complaint was photosensitivity. Her husband knows her HIV-positive status, but he refused to be tested. She claimed her husband had no health complaints at the time of her intake. We started her on LDN because her CD4 levels were erratic. She never developed IRIS and her CD4 count ranges from mid 800's to low 1000's. Patient admits she does not consistently use barrier protection because her partner becomes violent if she asks him to use condoms.

was sick, on-and-off. Despite being advised to continue HAART when she was enrolled in the instant experiment, she withdrew HAART for two weeks on her own initiative, and her CD4 plummeted. Applicants confronted her and she continued taking HAART+one HC+LDN daily. Her husband also decided to join the program. Her ALT has been consistently normal.

This patient did not develop IRIS despite the rapid increase in her CD4 at last observation about six and a half years after she initially tested HIV positive.

| E.N.1 ♀ | Start of treatment (Baseline) | 1 month of treatment | 3 months of treatment | 4 months of treatment | 5 months of treatment |
|---|---|---|---|---|---|
| Educ: Class 7 | | 1 cap TID = 25.4212.71 mg/kg/day | 1 cap BID = 8.5 mg/kg/day | 1 cap BID = 8.5 17 mg/kg/day | 1 cap BID = 8.5 17 mg/kg/day + LDN |
| CD4 Creatinine ESR | 895 cells/uL 0.6 mg/dl | 716 cells/uL 0.7 mg/dl ESR = 80 mm/hr | 1232 cells/uL 0.4 mg/dl ESR = 15 mm/hr | 990 cells/uL 1.2 mg/dl | 1376 cells/uL 0.5 mg/dl ESR = 10 mm/hr |

| E.N. 1 ♀ | Start of treatment Baseline | 1½ month of treatment | 1¾ months of treatment | 2 months of treatment | 3 months of treatment | 6 months of treatment |
|---|---|---|---|---|---|---|
| Educ: Class 6 | On ARVs, then discontinued HAART against advice. | 1HC = 6 mg/kg/day | HAART + 1HC OD = 6 mg/kg/day + LDN | HAART + 1 HC OD = 6 mg/kg/day + LDN | HAART + 1 HC OD = 6 mg/kg/day + LDN | HAART + 2 HC OD = 12 mg/kg/day + LDN |
| CD4 Creatinine ESR ALT | 1023 cells/uL 1.4 mg/dl; ALT-6.7 u/l | 198 cells/uL 0.7 mg/dl ESR = 14 mm/hr; ALT = 9.6 u/l | 211 cells/uL 1.0 mg/dl ESR = 6 mm/hr | 290 cells/uL 1.2 mg/dl ALT = 11.4 u/L | 415 cells/uL 1.0 mg/dl ESR = 8 mm/hr ALT = 8.5 u/L | 464 cells/μL |

B) E. N.2, a 25 year-old married mother, was initially tested HIV-positive through the Prevention of Mother to Child Transmission Program (PMTCT) of the Government of Kenya. She is from a residential area more than fifteen kilometers from the clinic. She wanted to hide her status from her husband because she admitted she had gotten the infection from another partner.

She was turned down several times to be a participant in the herbal program because she refused to take her husband for counseling. However, she was included because she cried, begged and did not want to leave the clinic unless she was included. She was diagnosed with borderline cardiomegaly around one year after initially testing HIV positive, and developed tachycardia, but had no subjective complaint and never developed fever. We maintained her on Lanoxin 250 μg, which controlled her heart rate below 100 beats/minute, and also started her on LDN.

She tested positive on a pregnancy test about two months after the start of treatment. We retained her despite her pregnancy, because her CD4 increased to 342 cells and her ESR dropped to 0 mm/hr after she was started on LDN, within a period of one month. She dropped out of the experiment one month later and returned after two months. She does not use any form of barrier protection, as her husband does not know she is HIV positive.

At last observation, she tested negative on Determine and weak positive on Bioline. She was lost to follow up when her husband found out her status.

| E.N.2 ♀ | Start of treatment Baseline | 1 month of treatment | 3 months of treatment | 4 months of treatment |
|---|---|---|---|---|
| Educ: Form 4 | | 2 caps TID = 60 mg/kg/day | 1 cap OD = 10 mg/kg/day | 1 cap OD + LDN = 10 mg/kg/day |
| CD4 Creatinine ESR | 521 cells/uL 0.7 mg/dl | 499 cells/uL 4.9 mg/dl ESR = 15 mm/hr | 418 cells/uL Not done ESR = 6 mm/hr | 760 cells/uL 0.5 mg/dl ESR = 0 mm/hr |

Example 4

Herbal Remedy+antiTB+LDN

A) G. K., a 32 year-old married female from Njenga, was initially diagnosed HIV positive in a hospital in Njenga. She was initially tested for HIV because she was ill. Patient was asymptomatic at the time of intake, but was diagnosed to have extra-pulmonary tuberculosis (pneumonia with left pleural effusion) through chest X-ray 5 months after therapy with the compositions of U.S. Pat. No. 7,556,830. She was X-rayed because her CD4 count failed to go up during the instant experiment, as expected. G. K. was started on anti-TB medications four days after the X-ray.

| G.K. ♀ | Start of treatment Baseline | 2½ month of treatment | 6½ months of treatment | 9½ months of treatment |
|---|---|---|---|---|
| Educ.: Class 8 | | 1 cap BID = 11 mg/kg/day | 1 cap OD = 5.5 mg/kg/day + Intensive Phase AntiTB = two months (INH, Rif, PZA & Etham) + LDN | 1 cap BID = 11 mg/kg/day + Continuation Phase Anti-Tb (INH + Rifampicin) = 3 months + LDN |
| CD4 Creatinine ALT | 565 cells/uL 0.78 mg/dl ALT = 13.4 μg/L | 465 cells/uL 1.0 mg/dl | 352 cells/uL ALT = 31.4 μg/L | 621 cells/uL 0.9 mg/dl |

Table 1 below summarizes the results of treatment showing the patients' variability in the stages of their HIV disease. The variability in the case histories of the patient demonstrates, inter ails, that the invention can be used to treat HIV in all stages of the disease and in the worst imaginable living conditions. The absence or presence of other co-morbid conditions have also been noted and provide data that the compositions of U.S. Pat. No. 7,556,830 and the HC form thereof combined with LDN are safe, and can be used while on anti-TB or HAART treatment or with any other antimicrobials. All subjects are currently receiving 1 HC twice daily (B.I.D. as defined above). All subjects except H. K are currently receiving one dose of LDN at bedtime. The foregoing is considered a preferred embodiment of the invention.

Table 1 is a summary report on all subjects of the instant experiment, comprising but not limited to the examples above.

TABLE 1

PRESENTATION OF CD4 COUNTS IN THE INSTANT EXPERIMENT

| Name | CD4 Baseline | Mo. 1 | Mo. 2 | Mo. 3 | Mo. 4 | Mo. 5 | Mo. 6 | Mo. 7 | Mo. 8 | Mo. 9 | Mo. 10 | Mo. 11 | Mo. 12 | Mo. 13 |
|---|---|---|---|---|---|---|---|---|---|---|---|---|---|---|
| 1. □ ©*J.A.1♀ | 399 | 265 | 268 | 262 | | 249 | 211 | ⁊ | | | | | | |
| 2. □ ©♠ ♥J.A.2♀ | 332 | 287 | 302 | 330 | 274 | 307 | 279 | 218 | 334 | ⁊ | | | | |
| 3. *R.A♀ | 895 | 716 | | 1232 | 990 | 1367 | 811 | 857 | 895 | 1239 | | | | |
| 4. ⁊*I.B. | 974 | 723 | 1308 | 717 | 698 | ⁊ | | | | | | | | |
| 5. * ©♠G.K.♀ | 563 | | | 467 | ♠ᵃ | | | 465 | 479 | 435 | 621 | 415 | 417 | |
| 6. ©ΨM.K.♀ | 180 | 245 | 255 | | | | | | | | | | | |
| 7. *♠R.K.♀ | 334 | 330 | 371 | | 352 | | 344 | | 371 | 399 | 374 | | | |
| 8. ⁱᴱ ‡H.K♂ | 556 | 477 | 554 | 578 | | 610 | 638 | | | | | | | |
| 9. ᵇ *ρ*N.M.♀ | 642 | 649 | ᵇ | ᵇᵃ | 625 | 851 | | | 683 | 725 | 675 | | | |
| 10. *♠νS.M.♀ | 721 | 995 | | 698 | 822 | 1112 | 647 | 1087 | 1004 | 1265 | 947 | 1005 | | |
| 11. P.M.♀ | 695 | 718 | 619 | | 870 | | 625 | | 762 | 699 | 829 | | | |
| 12. Φ⁕*∀S.M.♂ | 85 | | 88 | 78 | 69 | 147 | | | | | | | | |
| 13. *‡F.M.♀ | 432 | | | 322 | 295 | 358 | 476 | 437 | 823 | 525 | | | | |
| 14. ♥* M.M.♀ | 590 | 347 | 504 | 592 | | | | | | | | | | |
| 15. ♠♠*P.M.♂ | 556 | 431 | 447 | 448 | 468 | 434 | ♠°450 | 450 | 396 | 325 | 323 | 392 | | |
| 16. ᵇ ⁽ᵃ ρ*νE.M.♀ | 476 | | 547 | ᵇ | ᵇ | ᵇᵃ | 543 | ᵇᵃ | 575 | | 594 | | | |
| 17. □*T.M.♂ | 425 | | 404 | 664 | 462 | 500 | 337 | ⁊ | | | | | | |
| 18. *E.M.♀ | 575 | 341 | 558 | | 437 | 664 | 452 | 762 | 591 | 629 | | | | |
| 19. ΘE.N.1♀ | 1023 | ⁿ | ⁿ | 198 | 211 | 290 | 415 | 411 | 464 | ⁿ 377 | 453 | | | |
| 20. □*♠ ♥E.N. 2♀ | 521 | 489 | | 418 | ᵇ | 760 | 893 | 571 | 562 | ⁊ | | | | |
| 21. ⁊B.N.♀ | ∀775 | 675 | 439 | 670 | 674 | 571 | 565 | 589 | 716 | ⁊ | | | | |
| 22. ‡*A.N.♀ | 402 | | | | | | 483 | 488 | | | | | | |
| 23. *F.N.♀ | 108 | 743 | 682 | | 920 | 555 | 579 | 530 | 566 | 915 | | | | |
| 24. ©UL.N.♀ | 483 | 559 | 335 | 351 | 464 | 475 | 468 | 328 | 3541 | | | | | |
| 25. ±* © νM.N.♀ | 602 | 359 | 438 | 344 | 313 | 293 | 359 | 401 | 247 | | | | | |
| 26. ±*N.O.♀ | 267 | 253 | 223 | 212 | 141 | | | | | | | | | |
| 27. ±*♥♠ S.O.♂ | 215 | 124 | ⊥118 | | | 58 | 19 | 8 | 3 | 6 | | | | |
| 28. ©ᴿ C.O. | 464 | 1027 | 433 | 731 | 997 | 977 | 1154 | 852 | 1009 | 849 | 784 | | | |
| 29. *s.s.♀ | 216 | 156 | 133 | 134 | 187 | 154 | 195 | | | | | | | |
| 30. ©ᵇᵃᵇᵃᵇ *L.V.♀ | 214 | 227 | 234 | ᵇᵃ | ᵇᵃ250 | | 301 | ᵇ233 | 277 | 243 | | | | |
| 31. □*G.W.♂ | 357 | | 116 | 146 | | | | | | | | | | |
| 32. ©*M.W.1♀ | 671 | 1107 | 781 | 669 | 758 | ∀590 | 1045 | 637 | 750 | | | | | |
| 33. ♠°*N.W.♀ | 211 | 237 | 282 | ♠°113 | 195 | 146 | 307 | | | | | | | |
| 34. ♠°§ ©* ν M.W. 2♀ | 132 | 128 | | ♠°130 | 167 | 315 | | | | | | | | |

Symbols Used in Table 1:
♀ Female;
♂ Male;
□ Lost to follow up;
ᵇ Pregnancy;
* Does not use/inconsistently use barrier protection;
ᵇᵃ Pregnancy aborted;
♠ Active TB case diagnosed during LDN therapy;
♠° TB Treatment - Intensive Phase started;
♠ Old TB case;
ᴿ Recurrent malaria;
♥ Cardiomegaly or highly suggestive of carditis but afebrile;
Θ On HAART;
© Chronic urinary tract infection;
ⁿ Patient discontinued HAART against advice;
Φ Father of suspected incest victim;
U Severe uterine prolapse;
Ψ Suspected incest case, fourteen years-old, both parents are HIV-positive;
ν Sent for vocational training;
∀ Amebiasis;
‡ Herpes lesions resolved;
Φ Father of suspected incest victim;
§ Severe genital warts;
± Advised to start HAART. Treatment failure. Patient insists on not using barrier protection;
ρ Probably a prostitute = pregnancy + no partner/spouse + no job + no skills + with children.
Notes on Table 1:
All subjects are residents live in Mukuru except for E.N.2.
All subjects receive the herbal composition (HC) and LDN, except for H.K., who receives only the HC.
A blank space denotes that a patient was unable to come for lab tests.
No subject receives HAART except E.N.1.

The administration of an effective remedy without side-effects is always the ideal goal for any therapy. Unfortunately, at this point enough data has been collected that to show that the use of HAART has not lived up to all of the initial expectations concerning it. Especially in a resource-poor setting where the only free testing for the presence of tuberculosis infection has been limited to Mantoux test and sputum exam, the probability of diagnosis of tuberculosis remains low despite its high incidence in the population. Further, discontinuing and restarting a patient on HAART while the patient commences TB treatment could well cause a mutation in the virus, requiring a switch to another HAART cocktail combination when the HAART therapy is restarted, and creates the possibility of new side-effects.

Our use of the instant invention at any stage of the HIV disease, with or without the presence of treatment for other opportunistic infections, shows the safety and effectiveness of the invention alone and in combination with anti-TB drugs, antiretrovirals and other antimicrobials, making the instant invention the drug of choice in HIV treatment.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, which are defined by the scope of the claims in the light of the specification.

Definitions provided herein are not intended to be limiting from the meaning commonly understood by one of skill in the art unless indicated otherwise.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the gene description of the invention with a proviso or negative limitation removing any subject matter from the genus, regardless of whether or not the excised material is specifically recited herein.

The plant parts described in the specification of U.S. Pat. No. 7,556,830 are those in which, in the experience of the Applicants, the highest concentration of beneficial ingredients are to be found. However, it will be apparent to those skilled in the art that the same or other beneficial compounds may be found in other parts of the recited plants not specifically recited in the above application, that the dosages recited elsewhere in this application are variable, and that therefore, any composition comprised of any part or parts of the recited plants which includes *Dovyalis abyssinica* and *Clutia robusta* and/or the alkaloid compounds of U.S. Patent Application Publication No. 2009-0069277 A1, plus naltrexone is within the scope of the invention.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCES

1. Abouya Y L, Beaumel A, Lucas S, Dago-Akribi A, Coulibaly G, N'Dhatz M, Konan J B, Yapi A, et al. *Pneumocystis carinii* pneumonia. An uncommon cause of death in African patients with acquired immunodeficiency syndrome. *Am Rev Respir Dis.* 1992 March; 145(3):617-20. Available at http://www.ncbi.nlm.nih.gov/pubmed/1312314.
2. AIDS Education and Training Center—National AIDS Education and Training Centers National Resource Center. *Clinical Manual for Management of HIV-infected Adult: Testing and Assessment. 2006 Edition.* Taken from http://aidsetc.org.
3. Alòs L, Navarrete P, Morente V, et al. Immunoarchitecture of lymphoid tissue in HIV-infection during antiretroviral therapy correlates with viral persistence. *Modern Pathology.* 2005; 18:127-136. Taken from http://www.nature.com/modpathol/journal/v18/3800267a.html.
4. Antiretroviral drug. Wikepedia, the free encyclopedia website. Available at http://en.wikepedia.org/wiki/Antiretroviral_drug.
5. Canessa A, Del Bono V, De Leo P, Piersantelli, Terragna A. Cotrimoxazole therapy of Toxoplasma gondii in AIDS patient [abstract]. *Eur J Clin Microbiol Infect Dis.* 1992; 11: 125-30. Taken from http://wwwaidshivreaserch.com.
6. Choi A, Rodriguez R. Renal Manifestations of HIV. *UCSF HIV InSite.* November 2003; updated January 2008. Taken from http://hivinsite.ucsf.edu/InSite?page=kb-04-01-10.
7. Cohen J. Therapies: Confronting the Limits of Success. *Science AAS [American Association for the Advancement of Science] (serial online).* Taken from http://www.aidscience.org/Science/2320.html.
8. Co-trimoxazole. Wikepedia, the free encyclopedia website. Available at http//enwikepedia.org/wiki/Bactrim. Accessed Jun. 14, 2010.
9. Ganong W. Review of Medical Physiology. $17^{th}$ ed. Appleton & Lange, Norwalk, Conn.; 1995.
10. Githui W. A., et al. Improved diagnosis of Ziehl-Neelsen Smear Negative Tuberculosis Using sodium Hypochlorite Sedimentation Method. *East African Medical Journal.* October 2007, Vol. 89, No. 10. Pages 455-49.
11. Jacobson D., Slamovits T. Erythrocyte Sedimentation Rate and Its Relationship to Hematocrit in Giant Cell Arteritis. *Arch Ophthalmo. Vol.* 105, July 1987. Available at http://www.archophthalmol.com.
12. Kaposi's sarcoma. Wikepedia, the free encyclopedia website. Available at http://en.wikipedia.org/wiki/Kaposi's_sarcoma.
13. Katzung B. Opioid Analgesics & Antagonists. *Basic and Clinical Pharmacology.* $10^{th}$ ed. The McGraw-Hill Companies, Inc.; 2007.
14. Low Dose Naltrexone (LDN) Homepage. Available at http://www.lowdosenaltrexone.org. Accessed Feb. 29, 2010.
15. Lechtzin N. HIV Guide—Zambia: *Pneumocystis carinii* pneumonia. *Online Johns Hopkins Point of Care Information Technology (serial online).* Available at http://www.zambiahivguide.org. Oct. 8, 2009.
16. Mallory J, Chalebois E, Morin S F, et al. Perceived Adverse Effects of Antiretroviral Therapy. *Journal of Pain and Symptom Management.* Vol. 29; 2:193-205 February 2005. Available at http:www.jpsmjournal.com/article/PIIS0885392404005299/full text.

17. McCandless J, Zimmerman J. Preventing AIDS with LDN in Mali, Africa. Available at http://www.ldnafrica-aids.org. Accessed May 20, 2010.
18. Moore E. Immunomodulatory and Biochemical Effects of LDN. *Benefits of Low Dose Naltrexone*. Available at http://autoimmune.suite101.com/article.cfm/benefits_of_low_dose_naltrexone.
19. Mcphee S, Papadakis M. HIV Infection and AIDS. 2010 *Current Medical Diagnosis and Treatment*. 49th ed. McGraw-Hill Companies, Inc; 2010:1205-1239.
20. Murdoch D M, Venter W, Van Rie A, Feldman C. Immune Reconstitution Inflammatory Syndrome (IRIS): Review of Common Infectious Manifestations and Treatment Options. *AIDS Research and Therapy* 2007, 4:9. Available at http://www.aidsrestherapy.com/content/4/1/9.
21. Ratnam I, Chiu C, Easterbrook. Incidence and Risk Factors for Immune Reconstitution Inflammatory Syndrome in an Ethnically Diverse HIV Type-1 Infected Cohort. HIV/AIDS. CID 2006:42 (1 February).
22. Republic of Kenya Ministry of Health. A Concise and Practical Guide to ARV Provision. *Kenyan National Clinical Manual for ARV Provider*. April 2004. First edition.
23. Rogers J, Zakaria S, Thom K A, Flammer K, Kanno M, Mehra M R. Immune Reconstitution Inflammatory Syndrome and Human Immunodeficiency Virus-Associated Myocarditis [Case Report]. *Mayo Clin Proc*. November 2008; 83(11): 1275-1279. Available at http:www.mayoclinicproceedings.com.
24. Ruskin J, LaRiviere M. Low-dose co-trimoxazole for prevention of *Pneumocystis carinii* pneumonia in Human Immunodeficiency Virus Disease [abstract]. *Lancet*. 1991 February 23:337(8739):468-71. PubMed U.S. National Library of Medicine National Institute of Health. Available at http://www.ncbi.nlm.nih.gov/pubmed/1671479. Accessed Jun. 15, 2010.
25. Sample I. Blanket HIV Testing 'could see AIDS' Dying Out in 40 years. guardian.co.uk. Feb. 21, 2010. Available at http:guardian.co.uk/world/2010/feb/21/blanket-testing-hiv-aids/print.
26. Shiel C. Antinuclear Antibody Test. MedicineNet.com [serial online]. Available at http://www.medicinenet.com/script/main/art.asp?articlekey 7083&pf=3&page=1.
27. U.S. Pat. No. 7,556,830.
28. U.S. Pat. No. 7,674,483.
29. U.S. Published Patent Application No. 2009-0069277 A1.

What is claimed is:

1. A pharmaceutical composition comprising:
a root extract of *Dovyalis abyssinica*;
a root extract of *Clutia robusta*; and
naltrexone.

2. The pharmaceutical composition of claim 1, further comprising an extract selected from the group consisting of stem bark of *Prunus Africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, root of *Periploca linearifolia* and mixtures thereof.

3. The pharmaceutical composition of claim 1, further comprising an extract of stem bark of *Prunus Africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

4. The pharmaceutical composition of claim 1, comprising dried root extract of *Dovyalis abyssinica*, or dried root extract of *Clutia robusta*.

5. The pharmaceutical composition of claim 2, comprising an extract selected from the group consisting of dried stem bark of *Prunus Africana*, dried stem bark of *Croton macrostachyus*, dried stem bark of *Acacia nilotica*, dried root of *Rhamnus prunioides*, dried root of *Adenia gummifera*, dried root of *Asparagus africanus*, dried stem bark of *Anthocleista grandiflora*, dried whole plant of *Plantago palmata*, dried root of *Clematis hirsuta*, dried stem bark of *Ekebergia capensis*, dried stem bark of *Bersama abyssinica*, dried root of *Periploca linearifolia* and mixtures thereof.

6. The pharmaceutical composition of claim 1, wherein the root extract of *Dovyalis abyssinica* and the root extract of *Clutia robusta*, whether dried or not, are in a weight ratio of 1:1.

7. The pharmaceutical composition of claim 3, wherein the root extract of *Dovyalis abyssinica*, the root extract of *Clutia robusta*, the stem bark extract of *Prunus africana*, the stem bark extract of *Croton macrostachyus*, the stem bark extract of *Acacia nilotica*, the root extract of *Rhamnus prinoides*, the root extract of *Adenia gummifera*, the root extract of *Asparagus africanus*, the stem bark extract of *Anthocleista grandiflora*, the whole plant extract of *Plantago palmata*, the root extract of *Clematis hirsuta*, the stem bark extract of *Ekebergia capensis*, the stem bark extract of *Bersama abyssinica* and the root extract of *Periploca linearifolia*, whether dried or not, are in a weight ratio of 2:2:2:2:2:2:1:2:2:1:2:2:2:2.

8. The pharmaceutical composition of claim 1, having an amount of extract of approximately 250 mg.

9. The pharmaceutical composition of claim 1, wherein the extract is a water extract.

10. The pharmaceutical composition of claim 1, wherein the amount of naltrexone is 0.1 mg to 10 mg.

11. A method for preparing a pharmaceutical composition comprising the steps of:
a) obtaining a mixture of the extract of claim 9;
b) boiling the mixture from step a) in water;
c) filtering the water extract of step b) to obtain a filtrate;
d) adding naltrexone; and
e) preparing the pharmaceutical composition from the resulting mixture.

12. A method of treating AIDS in a patient comprising administering to the patient a pharmaceutical composition comprising a therapeutically effective amount of the composition of claim 1.

13. The method of claim 12, wherein the pharmaceutical composition further comprises an extract selected from the group consisting of stem bark of *Prunus Africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, root of *Periploca linearifolia* and mixtures thereof.

14. The method of claim 12, wherein the pharmaceutical composition further comprises an extract of stem bark of *Prunus Africana*, stem bark of *Croton macrostachyus*, stem bark of *Acacia nilotica*, root of *Rhamnus prunioides*, root of *Adenia gummifera*, root of *Asparagus africanus*, stem bark of *Anthocleista grandiflora*, whole plant of *Plantago palmata*, root of *Clematis hirsuta*, stem bark of *Ekebergia capensis*, stem bark of *Bersama abyssinica*, and root of *Periploca linearifolia*.

15. The method of claim 12, wherein the pharmaceutical composition comprises a therapeutically effective amount of dried root extract of *Dovyalis abyssinica*, or dried root extract of *Clutia robusta*.

16. The method of claim 13, wherein the pharmaceutical composition comprises a therapeutically effective amount of dried stem bark extract of *Prunus Africana*, dried stem bark extract of *Croton macrostachyus*, dried stem bark extract of *Acacia nilotica*, dried root extract of *Rhamnus prunioides*, dried root extract of *Adenia gummifera*, dried root extract of *Asparagus africanus*, dried stem bark extract of *Anthocleista grandiflora*, dried whole plant extract of *Plantago palmata*, dried root extract of *Clematis hirsuta*, dried stem bark extract of *Ekebergia capensis*, dried stem bark extract of *Bersama abyssinica*, or dried root extract of *Periploca linearifolia*.

17. The method of claim 12, wherein the root extract of *Dovyalis abyssinica* and the root extract of *Clutia robusta*, whether dried or not, are in a weight ratio of 1:1.

18. The method of claim 14, wherein the root of *Dovyalis abyssinica*, the root of *Clutia robusta*, the stem bark extract of *Prunus africana*, the stem bark extract of *Croton macrostachyus*, the stem bark extract of *Acacia nilotica*, the root extract of *Rhamnus prinoides*, the root extract of *Adenia gummifera*, the root extract of *Asparagus africanus*, the stem bark extract of *Anthocleista grandiflora*, the whole plant extract of *Plantago palmata*, the root extract of *Clematis hirsuta*, the stem bark extract of *Ekebergia capensis*, the stem bark extract of *Bersama abyssinica* and the root extract of *Periploca linearifolia*, whether dried or not, are in a weight ratio of 2:2:2:2:2:2:1:2:2:1:2:2:2:2.

19. The method of claim 12, wherein the pharmaceutical composition comprises an amount of extract of approximately 250 mg.

20. The method of claim 12, wherein the extract is a water extract.

21. The method of claim 12, wherein the amount of naltrexone administered is 0.1 mg to 10 mg.

* * * * *